United States Patent
Cleary et al.

(10) Patent No.: US 7,361,754 B2
(45) Date of Patent: Apr. 22, 2008

(54) GENETICALLY PURIFIED GELLAN GUM

(75) Inventors: Joseph M. Cleary, Carlsbad, CA (US); Russell J. Coleman, San Diego, CA (US); Nancy E. Harding, San Diego, CA (US); Yamini N. Patel, San Diego, CA (US)

(73) Assignee: CP Kelco US, Inc., Atlanta, GA (US)

( * ) Notice: Subject to any disclaimer, the term of this patent is extended or adjusted under 35 U.S.C. 154(b) by 0 days.

(21) Appl. No.: 11/156,953

(22) Filed: Jun. 20, 2005

(65) Prior Publication Data

US 2006/0003051 A1  Jan. 5, 2006

Related U.S. Application Data

(60) Provisional application No. 60/580,730, filed on Jun. 21, 2004.

(51) Int. Cl.
*C07G 17/00* (2006.01)
*C12N 1/20* (2006.01)
*C12N 15/87* (2006.01)
*C09K 3/00* (2006.01)
*A23C 9/154* (2006.01)
*A23C 9/12* (2006.01)

(52) U.S. Cl. .................. 536/114; 426/34; 426/580; 426/36; 435/252.3; 435/463; 516/105

(58) Field of Classification Search .............. 426/34, 426/580; 435/69.1, 252.34
See application file for complete search history.

(56) References Cited

U.S. PATENT DOCUMENTS 6,602,996 B1 * 8/2003 Sworn et al. ............... 536/114
6,663,911 B2 * 12/2003 Valli et al. .................. 426/580

OTHER PUBLICATIONS

Coleman et al., Organization of genes required for gellan polysaccharide biosynthesis in *Sphingomonas elodea* ATCC 3146. J. Indust. Microbiol. & Biotechnol., 2004, pp. 1-26.*

* cited by examiner

*Primary Examiner*—Rebecca E. Prouty
*Assistant Examiner*—Ganapathirama Raghu
(74) *Attorney, Agent, or Firm*—Sarah A. Kagan; Patricia Ades; Jane Shershenovich

(57) ABSTRACT

Mutational inactivation of proteins involved in para-cresol production in certain milk products results in improved taste and odor. The undesirable para-cresol forms over time as a result of enzymes produced by the bacterium that produces gellan gum. Since the gellan is typically used in a relatively unpurified form, the enzymes are added to the milk along with the gellan. Inactivation of the enzymes is a genetic means of eliminating the enzymes without requiring any additional purification or processing.

6 Claims, 2 Drawing Sheets

GENETICALLY PURIFIED GELLAN GUM

This application claims priority under 35 U.S.C. 119(e) to provisional application 60/580,730 filed on Jun. 21, 2004.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The invention relates to the field of food additives. In particular it relates to the field of dairy food additives. More particularly it relates to additives to sterilized milk products.

BACKGROUND OF THE INVENTION

Gellan gum is an extracellular polysaccharide produced by the bacteria *Sphingomonas elodea*. Gellan gum produced by *S. elodea* is commercially available as Kelcogel LT100® from CP Kelco, San Diego, Calif. Commercially, gellan gum is formed by aerobic fermentation. Upon completion of fermentation, the broth is pasteurized to kill viable cells prior to recovery of the gum from the fermentation broth.

Gellan gum comprises the sugars glucose, glucuronic acid, and rhamnose in a 2:1:1 molar ratio, which are linked to form a tetrasaccharide repeat unit. Native gellan gum is acetylated and glycerylated on the same glucose residues. On average, there is one acetyl group and one half glyceryl group per tetrasaccharide repeat unit.

The method of recovery of the gellan gum affects the characteristics of the gum. Direct recovery yields a soft, flexible gel. Gellan gum has long been used in cultured, retorted, and frozen dairy products due to its textural and rheological properties. However, an off-flavor and odor develop in otherwise shelf-stable, milk-based, gellan-containing products; this flavor and odor render the foods unpalatable. The off-flavor and odor have been linked to the formation of para-cresol from substrates in milk, e.g., para-cresyl sulfate and para-cresyl glucouronide. Para-cresol is detectable in milk-based, gellan-containing products that have been treated at ultra high temperatures and stored at room temperature.

In an effort to eliminate this problem, gellan has been deacylated with hot alkali treatment. While effective in eliminating the para-cresol, the deacylation processing makes the gellan gum more brittle and less useful for certain food applications. Another approach to eliminate this problem is the pre-treatment of native gellan gum with a denaturing agent, such as sodium hypochlorite or potassium hydroxide. This approach adds material and processing costs. There is a need in the art for a gellan product which does not produce para-cresol upon prolonged storage in a sterilized dairy product and which does not require extra processing steps.

BRIEF SUMMARY OF THE INVENTION

In a first embodiment a composition is provided which comprises gellan gum substantially free of arylsulfatase protein.

In a second embodiment a composition is provided which comprises gellan gum substantially free of β-glucuronidase protein.

In a third embodiment of the invention a composition is provided which comprises gellan gum substantially free of both arylsulfatase and β-glucuronidase proteins.

In a fourth embodiment of the invention a method is provided for producing a gellan gum composition. *Sphingomonas elodea* is cultured in a culture medium. The *Sphingomonas elodea* produces no catalytically active arylsulfatase, or no catalytically active β-glucuronidase, or no catalytically active arylsulfatase and no catalytically active β-glucuronidase. The culture medium is collected. Gellan gum is precipitated from the culture medium.

A microbiologically pure culture of *Sphingomonas elodea* is provided in a fifth embodiment of the invention. It is arylsulfatase-deficient.

Another microbiologically pure culture of *Sphingomonas elodea* is provided in a sixth embodiment of the invention. It is β-glucuronidase-deficient.

Still another embodiment of the invention is a microbiologically pure culture of *Sphingomonas elodea*. It is deficient in both arylsulfatase and β-glucuronidase.

An eighth embodiment of the invention provides an isolated and purified polynucleotide encoding a *Sphingomonas elodea* arylsulfatase. The arylsulfatase has an amino acid sequence according to SEQ ID NO: 2.

A ninth embodiment of the invention provides an isolated and purified polynucleotide encoding a *Sphingomonas elodea* β-glucuronidase. The β-glucuronidase has an amino acid sequence according to SEQ ID NO: 5.

A tenth embodiment of the invention is an isolated and purified polynucleotide comprising *Sphingomonas elodea* genomic DNA. The genomic DNA comprises a deletion of all or part of its arylsulfatase coding sequence.

An eleventh embodiment of the invention is an isolated and purified polynucleotide comprising *Sphingomonas elodea* genomic DNA. The genomic DNA comprises a deletion of all or part of its β-glucuronidase coding sequence.

These and other embodiments of the invention as described in more detail below provide the art with cost-effective means to make a more consumer-acceptable, sterilized, gellan-containing, dairy product.

DETAILED DESCRIPTION OF THE INVENTION

Figure 1:
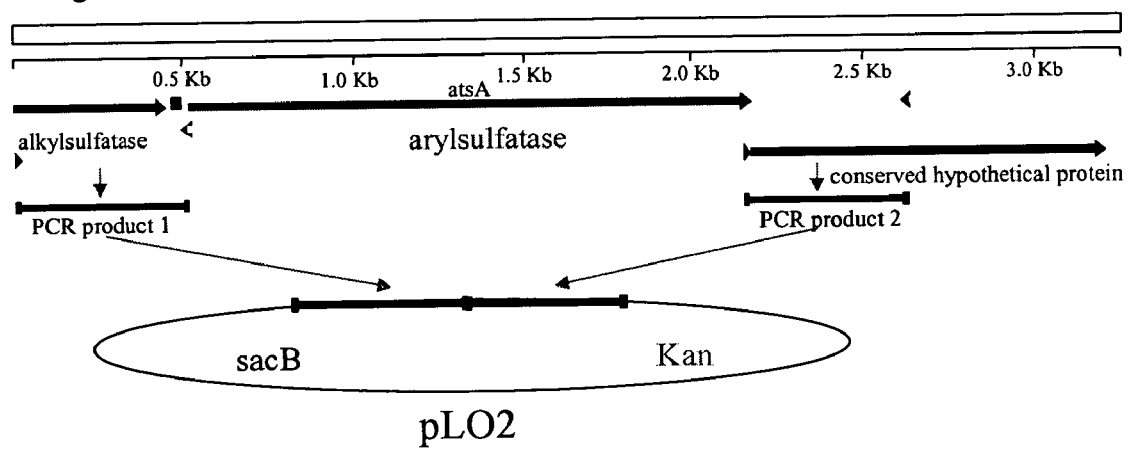
FIG. 1. Genetic map of the genomic region around the arylsulfatase gene (atsA) and location of the regions amplified by PCR and cloned into plasmid pLO2. Plasmid pLO2 with the cloned PCR fragments was then used to replace this region of the genome with the deletion, by homologous recombination.

The present inventors have found that if either of the genes encoding the enzymes arylsulfatase and β-glucuronidase or both genes are mutationally inactivated in the bacterium *Sphingomonas elodea*, the bacterium produces a gellan that has superior properties for certain purposes. In particular, the gellan that is produced by such mutants imparts to sterilized milk products a longer shelf-life.

If one or both of the enzymes are not inactivated then they produce para-cresol from substrates (p-cresyl-sulfate and p-cresyl-glucuronide) found in the milk. The para-cresol imparts an odor and flavor that is generally unpalatable to consumers. Eliminating these enzymes reduces the rate at which para-cresol is produced in the sterilized milk or milk product on the shelf.

Mutations in either or both of the enzymes may be used to reduce the rate of para-cresol production. The mutations are preferably of the type that totally inactivates the protein, such as insertions, nonsense, frameshift, or deletion mutations. Any technique known in the art for producing such mutations may be used. The applicants used a transposon insertion strategy to identify the genes encoding arylsulfatase and β-glucuronidase. A deletion mutation in each gene was then constructed by homologous recombination using 5' and 3' DNA fragments flanking the gene which were joined together. Nonetheless, other strategies can be used to obtain the mutations in these genes. The mutations can be made directly in a gellan "production" strain, or the mutations can be transferred to such a strain from a strain in which the mutation is first made. Techniques for site-directed mutagenesis are well known in the art. See, e.g., "In Vitro Mutagenesis Protocols, second edition, Braman, Jeff, ed., Humana Press, 2002, and the commercially available QuikChange™ kit (Stratagene). Provided with the wild-type sequences of the *S. elodea* arylsulfatase and β-glucuronidase genes, one of skill in the art can readily make a variety of desired mutations in these genes.

The sequence of the wild-type and mutant genes encoding arylsulfatase and β-glucuronidase have been determined. See SEQ ID NO: 1 (wild-type arylsulfatase), SEQ ID NO: 3 (deletion of arylsulfatase), SEQ ID NO: 4 (wild-type β-glucuronidase), and SEQ ID NO: 6 (deletion of β-glucuronidase). The identification of these genes and their nucleotide sequences permits one of skill in the art to readily make other mutations having the desired null phenotype for expression of these enzymes. Mutations such as insertions, deletions, nonsense, and frameshift are most likely to result in a null phenotype for the enzymes. Missense mutations can also be made and routinely tested for their effect on enzyme activity. Standard techniques of microbial genetics can be used to make suitable mutations. See, e.g., *Principles of Gene Manipulation: An Introduction to Genetic Engineering*, R. W. Old, S. B. Primrose, Blackwell Publishing, 1994. Standard enzyme assays can be used to test for loss of activity of the mutated enzymes. See, e.g., Kim et al., *Appl Microbiol Biotechnol.* 2004 February; 63(5):553-9.

Compositions of the present invention which are substantially free of arylsulfatase or β-glucuronidase contain less than 95%, 96%, 97%, 98%, or 99% of the amount of the particular protein than is contained in wild-type strains. Such a reduction in amount of enzyme should lead to sterilized milk compositions which have less than 90%, 93%, 95%, 97%, or 99% of the amount of para-cresol that is produced in compositions containing gellan from wild-type strains. The amount of arylsulfatase or β-glucuronidase protein which is produced can be measured by enzyme assay using a readily assayable substrate such as 5-bromo-4-chloro-3-indolyl sulfate (X—SO4); CAS No. 6578-07-0 from Sigma or using 5-bromo-4-chloro-3-indolyl-β-D-glucuronide (X-GlcA); CAS No. 114162-64-0, from Sigma or RPI Corp. or using p-nitrocatechol. Alternatively the protein can be measured using an immunological technique such as a Western blot.

Gellan gum is typically used in sterilized or ultra high temperature (UHT) treated dairy products or frozen dairy products. Such products include without limitation, ice cream, frozen yogurt, pudding, whipped dairy product, coffee creamer, crème brulee, and dairy beverages. The gellan gum of the present invention can be used in these or any other foods as can typical gellan from a wild-type strain. Gellan gum is typically used for suspension of fine particles, but it also can be used to impart a favorable mouth feel.

Gellan gum can be produced using the mutant strains of the present invention according to any of the methods known in the art for wild-type strains. The bacteria are typically grown in a liquid culture medium. Such medium typically contains a carbon source, phosphate, organic and inorganic nitrogen sources, and appropriate trace elements. The fermentation is typically conducted under sterile conditions, with aeration and agitation. At the end of the fermentation period, the culture medium is collected, typically without removing the cells. The fermentation broth can be pasteurized to kill viable cells prior to recovery of the gellan gum. The gellan gum can be precipitated as is known in the art. Typically this is done with an alcohol, such as isopropanol. The precipitated gellan can be dried prior to rehydration.

Para-cresol can be measured by any means known in the art. One method which can be used employs dichloromethane extraction, concentration, and gas chromatographic-mass spectroscopy.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

EXAMPLES

Example 1

The following reagents were used in screening and characterizing mutant strains:
  5-bromo-4-chloro-3-indolyl sulfate (X—$SO_4$); CAS No. 6578-07-0 Source: Sigma.
  5-bromo-4-chloro-3-indolyl-β-D-glucuronide (X-GlcA); CAS No. 114162-64-0, Source: Sigma or RPI Corp.

Example 2

The genes encoding arylsulfatase and β-glucuronidase were identified by making a library of random transposon mutants in a nonrmucoid strain of *S. elodea*, Gps2, using the commercially available EZ::TN™ <R6 Kgamma-ori/KAN-2> insertion kit from Epicentre (Madison, Wis.). Kanamycin resistant mutant strains were screened for lack of (or significantly reduced) blue color on selective media with specific chromogenic substrates. See Example 1. Mutants blocking arylsulfatase production or activity were identified using the chromogen 5-bromo-4-chloro-3-indolyl sulfate (X—SO4) on agar with a defined medium with chloride salts. Mutants of β-glucuronidase were selected on a defined medium with the chromogen 5-bromo-4-chloro-3-indolyl-β-D-glucuronide (X-GlcA).

The transposon and adjacent genomic DNA were subsequently excised from the chromosome using restriction enzymes. The restriction enzyme fragments were circularized with ligase and transformed into *Escherichia coli* where the transposon-containing DNA can replicate due to presence of a replicon in the transposon. Plasmid DNA was purified and sequenced. The plasmid with the gene for arylsulfatase was designated R6K-AS#14E. A portion of this plasmid has been sequenced (SEQ ID NO: 1). The plasmid with the gene for beta-glucuronidase was designated R6K-BG#6S. A portion of this plasmid has been sequenced (SEQ ID NO: 4.) These plasmids in *Escherichia coli* strain EC100D pir+ are being deposited at the American Type Culture Collection, Manassas, Va., on Jun. 21, 2004.

In the bacterium that had an inactivated arylsulfatase, the transposon had actually inserted in a gene for a hypothetical protein that was adjacent to the gene for arylsulfatase. In the bacterium that had an inactivated β-glucuronidase, the transposon insertion was located in the amino portion of the gene for β-glucuronidase. DNA sequencing of the genes showed that they were homologous to known genes from other species in the database of the National Center for Biotechnology Information (NCBI).

The genes for arylsulfatase and β-glucuronidase and adjacent genomic DNA were sequenced. Deletions of the genes were constructed on a plasmid and then transferred into *S. elodea* strains S-60 wtc and PDG-1. See WO 01/64897. The deletions were inserted in the genome by homologous recombination. DNA sequences flanking the target gene were amplified by PCR and cloned into the plasmid vector pLO2. (Lenz, O., E. Schwartz, J. Demedde, M. Eitinger and B. Friedrich. 1994, "The *Alcaligenes eutrophus* H16 hoxX gene participates in hydrogenase regulation," *J. Bacteriol.* 176:4385-4393.) This construct was transferred into the *S. elodea* strain by conjugation. The resulting kanamycin resistant strains were then grown for 30-40 generations in the absence of antibiotic. Isolates that had lost the plasmid were detected by selection for sucrose tolerance due to loss of the sacB gene on pLO2, and confirmed by kanamycin sensitivity. Isolates that had lost the plasmid after the non-selective growth were of two types, deletion or wild-type. The desired deletion strains were identified by lack of blue color on appropriate indicator agar (see example 1) and by diagnostic PCR. The scheme for construction is shown in FIG. 1 below.

To construct a precise deletion of the gene (atsA) for arylsulfatase it was necessary to determine the most likely start codon for the atsA gene and the start and stop codons of the adjacent genes. The locations of the ends of the genes were determined based on DNA sequences, homologies to other genes in GenBank and third base GC preference using the FramePlot-3 program. Ishikawa and Hotta. "FramePlot: a new implementation of the Frame analysis for predicting protein-coding regions in bacterial DNA with a high G+C content." *FEMS Microbiology Letters* 174:251-253 (1999). This analysis indicated that the arylsulfatase gene is translationally coupled to the gene for the conserved hypothetical protein, i.e., the stop codon of the arylsulfatase gene overlaps with the start codon of the gene for the conserved hypothetical protein. The arylsulfatase deletion was constructed to leave the alkylsulfatase gene and the gene for the unknown protein intact, since it is not known whether these proteins are required for optimal cell growth and gellan production.

Figure 2:
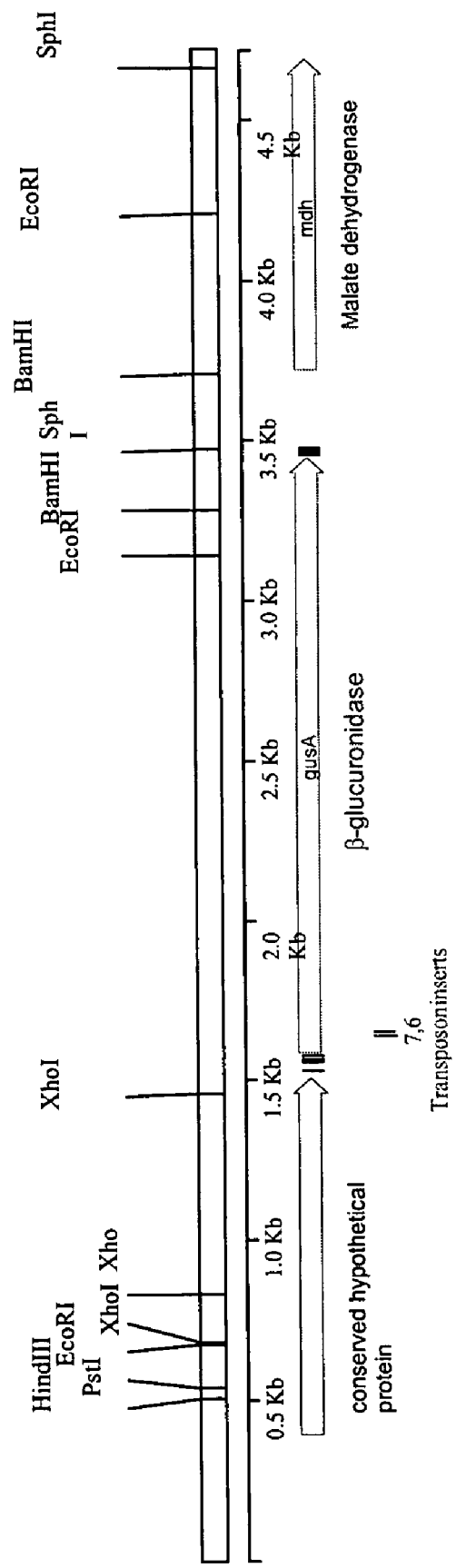
FIG. 2. Restriction map of the genomic region around the beta-glucuronidase gene (gusA) of *Sphingomonas elodea*. Positions of transposon insertions in clones BG-6 and BG-7 are indicated at the bottom.

PCR primers AS5 (CCGAGCTCAACGCCTTCGACTA TGTCCA; SEQ ID NO: 11) and AS6 (CCTCTAGA CTGGGGATTGTCCGGAAAAG; SEQ ID NO: 12) were used to amplify a 512 bp fragment just upstream of the start codon of atsA as a SacI-XbaI fragment (total 528 bp). Primers AS3 (CGTCTAGATCCACCCCGGCGACCT TCCC; SEQ ID NO: 13) and AS4 (TATAGCATGCGGC GACCACGGGCTCCTCCTCA; SEQ ID NO: 14) were used to amplify a 479 bp fragment including the end of the atsA gene and the start of the conserved hypothetical protein as an XbaI-SphI fragment (total 497 bp). Thus, the stop codon of atsA was retained but the start codon was deleted, so no portion of the arylsulfatase protein should be synthesized. Restriction sites for cloning were added to the ends of the primers. The PCR fragments were ligated sequentially into the polylinker of plasmid vector pLO2, to form the deletion of the atsA gene. The upstream SacI-XbaI fragment was cloned into SacI-XbaI cut pLO2. Subsequently the downstream XbaI-SphI fragment was cloned (FIG. 2). This plasmid with deletion of the atsA gene was transferred by conjugation into *S. elodea* strains S60 wtc and PDG-1 to allow recombination of the plasmid into the chromosome. Kanamycin resistant isolates were purified, then grown in the absence of antibiotic and plated on medium with sucrose and X—SO₄ to select isolates with sucrose tolerance due to loss of the plasmid-encoded sacB gene. Sucrose resistance, kanamycin sensitive, yellow colonies were selected. The atsA derivatives of S60 wtc and PDG-1 were designated GAS-1 and PAS-1 respectively.

A deletion of the gene (gusA) for β-glucuronidase was constructed on plasmid pLO2 and transferred into S60 wtc, GAS-1. The most likely start codon for the gusA gene was determined by homology to other proteins and the presence of ribosome binding sites. A region of secondary structure is upstream of the start codon. The deletion of the gusA gene was constructed to maintain secondary structures upstream and downstream of gusA. Primers Bgluc3 (AA CTGCAGACACGTGGCTTGTGCCGAAC; SEQ ID NO: 7) and Bgluc4 (GGCTCTAGACTTCTCCCTGTTCCTC CGGGAAA; SEQ ID NO: 8) were used to amplify a 560 bp fragment upstream of the gusA gene as a PstI-XbaI fragment (total 577 bp). Primers Bgluc1 (TTTCTAGATGACTGTC CAGGCCCCTCTC; SEQ ID NO: 9) and Bgluc2 (TC GAGCTCCAATGTCCTCGTAGCTGTTC; SEQ ID NO: 10) were used to amplify a 489 bp fragment downstream of gusA as an XbaI-SacI fragment (total 505 bp). The PstI-XbaI fragment was cloned into PstI-XbaI cut pLO2. Subsequently the downstream XbaI-SacI fragment was cloned. This plasmid with deletion of the gusA gene was transferred by conjugation into *S. elodea* strains S60 wtc, GAS-1 and PAS-1 to allow recombination. Kanamycin resistant isolates were purified, grown in the absence of antibiotic and then plated on media with sucrose and X-GlcA to select isolates with sucrose tolerance due to loss of the plasmid-encoded sacB gene. A mixture of blue-green (wild-type) and light green (mutant) colonies was obtained. Sucrose resistant, light green isolates were confirmed for plasmid loss by kanamycin sensitivity. The gusA deletion derivatives of S60 wtc, GAS-1 and PAS-1 were designated GBG, GBAD and PBAD respectively.

The deletion of the gene (atsA) for arylsulfatase in strains S60 wtc and PDG-1 has been completed. The gene for β-glucuronidase has been identified and sequenced. The adjacent DNA was sequenced. A deletion of the gene for β-glucuronidase has also been constructed in each of S60, PDG-1, and GAS-1.

Samples of gellan made from strains GAS-1 (with a deletion of the gene for arylsulfatase) and GBAD-1 (with deletions of genes for both arylsulfatase and β-glucuronidase) were evaluated for p-cresol production at monthly intervals in an ultra-high temperature dairy application test. Gellan samples from the wild-type strain produced 3 to 152 (average 65) ppb p-cresol after one month and 4 to 212 (average 96) ppb p-cresol after two months. Samples of gellan from GAS-1 produced about 1 to 3 ppb p-cresol after one to five months. Samples of gellan from GBAD-1 produced less than 1 ppb (limit of detection) when tested for up to three months.

We claim:

1. A composition comprising genetically purified gellan gum substantially free of catalytically active arylsulfatase protein and substantially free of denaturing agent and substantially free of denatured arylsulfatase protein.

2. A composition comprising genetically purified gellan gum substantially free of catalytically active β-glucuronidase protein and substantially free of denaturing agent and substantially free of denatured β-glucuronidase protein.

3. A composition comprising genetically purified gellan gum substantially free of catalytically active arylsulfatase and catalytically active β-glucuronidase proteins and substantially free of denaturing agent and substantially free of denatured arylsulfatase and β-glucuronidase protein.

4. The composition of claim 1 which is a culture broth of *Sphingomonas elodea*.

5. The composition of claim 1 which is a precipitated culture broth of *Sphingomonas elodea*.

6. The composition of claim 1 which is a sterilized milk product.

* * * * *

SEQUENCE LISTING

<160> NUMBER OF SEQ ID NOS: 14

<210> SEQ ID NO 1
<211> LENGTH: 3250
<212> TYPE: DNA
<213> ORGANISM: Sphingomonas elodea
<220> FEATURE:
<221> NAME/KEY: CDS
<222> LOCATION: (521)...(2176)

<400> SEQUENCE: 1

```
tccacaccaa cgccttcgac tatgtccagc aacgccccga ggcgaccagc gagcaggtcc      60
gccgtcaccg cgaagtgttc gcctccacgg cgtacgagac cgagcatccg gtggtgcgcg     120
tccatccggt gaccggcgag aagctgctgc tgctcggcag cttcgtgaag agcttcgtcg     180
ggttcagccg cgaggatttc tcccggctgt tcggcatcct gcaggatcat gcgaccaagc     240
ccgagaacac ggtgcgctgg cgctggagcc cgggcgatgt ggcgatctgg gacaaccgcg     300
ccacccagca ccgcgccatc gcggacttcg gcaagcacgc ccgccatctg cgccgggcga     360
cgatcgccgg cgacgtgccg cgcggcgtcg acggcaagcc cagccgggtg ctcaagcccg     420
agccggtcgc cgcagtcgaa gccgccgccg cctgaacttc ccgtgcctgg gccgcgctcc     480
cctcggggaa gcgcggctct cttttccgga caatccccag atg cgc ctt cgc ctc       535
                                             Met Arg Leu Arg Leu
                                              1               5 acc gcc ctg cta ctg ctg ctc ccc tcg ccg gcc gtg gtc gca cag            583
Thr Ala Leu Leu Leu Leu Leu Pro Ser Pro Ala Val Val Ala Gln
             10                  15                  20 gac aag ccc cac ccg gcc ccg ccc ccc aag cgc ccc aac atc ctg atc       631
Asp Lys Pro His Pro Ala Pro Pro Pro Lys Arg Pro Asn Ile Leu Ile
             25                  30                  35 atc gtc gcc gac gat ctc ggc tat tcg gac ctc ggc gcg ttc ggc ggc       679
Ile Val Ala Asp Asp Leu Gly Tyr Ser Asp Leu Gly Ala Phe Gly Gly
         40                  45                  50 gag atc cac acg ccc aat ctc gac gcg ctc gcc gag cac ggc ctg cgc       727
Glu Ile His Thr Pro Asn Leu Asp Ala Leu Ala Glu His Gly Leu Arg
     55                  60                  65 ctc acc ggc ttc cac gcc gcg ccg acc tgc tcg ccg acg cgc tcg atg       775
Leu Thr Gly Phe His Ala Ala Pro Thr Cys Ser Pro Thr Arg Ser Met
 70                  75                  80                  85 ctg ctg tcg ggc acc gac aac cac ctc gcg ggg ctc ggc aac atg gcc       823
Leu Leu Ser Gly Thr Asp Asn His Leu Ala Gly Leu Gly Asn Met Ala
                 90                  95                 100 gaa ctg gtc gcg ccc aac cag atc ggc aag ccc ggc tat cag ggc tat       871
Glu Leu Val Ala Pro Asn Gln Ile Gly Lys Pro Gly Tyr Gln Gly Tyr
             105                 110                 115 ctg ccc gac gac gtg gtg acg ctc gcc gag cgg ctg cgc gat ctc ggc       919
Leu Pro Asp Asp Val Val Thr Leu Ala Glu Arg Leu Arg Asp Leu Gly
         120                 125                 130 tat gca acc gcg atg tcg ggc aag tgg cat ctc ggc acg cgg ccg cag       967
Tyr Ala Thr Ala Met Ser Gly Lys Trp His Leu Gly Thr Arg Pro Gln
     135                 140                 145 gac gat ccc acc cgc cac ggc ttc gac cag gcc ttc acc ctg ctc cag      1015
Asp Asp Pro Thr Arg His Gly Phe Asp Gln Ala Phe Thr Leu Leu Gln
150                 155                 160                 165 ggc ggc gcc aac cat ttc ggc atc gat gcc acg gcg acc ccg ctg ccc      1063
Gly Gly Ala Asn His Phe Gly Ile Asp Ala Thr Ala Thr Pro Leu Pro
                 170                 175                 180
```

-continued

```
ggc cag gcg acc tat cgc gag aac ggc gtc acc ctg ccc aac ctg ccc      1111
Gly Gln Ala Thr Tyr Arg Glu Asn Gly Val Thr Leu Pro Asn Leu Pro
            185                 190                 195 aag gac ttc tat tcc tcc gac gcc tat gcc gcg aag ctg atc ggg ttc      1159
Lys Asp Phe Tyr Ser Ser Asp Ala Tyr Ala Ala Lys Leu Ile Gly Phe
        200                 205                 210 ctc ggc aag acg gac ccg gcc aag ccc ttc ttc gcc tat ctc acc ttc      1207
Leu Gly Lys Thr Asp Pro Ala Lys Pro Phe Phe Ala Tyr Leu Thr Phe
    215                 220                 225 acc gcg ccg cac tgg ccg ctt cag gca ctg ccc gag gat atc gcc aaa      1255
Thr Ala Pro His Trp Pro Leu Gln Ala Leu Pro Glu Asp Ile Ala Lys
230                 235                 240                 245 tat cgc ggc cgc tac gat gcc ggg ttc gag gtg ctc cag gcc gag cgg      1303
Tyr Arg Gly Arg Tyr Asp Ala Gly Phe Glu Val Leu Gln Ala Glu Arg
                250                 255                 260 ctg aag cgc cag cag gcg ctg ggg ctg gtg ccc gcg ggc gtg aag ccg      1351
Leu Lys Arg Gln Gln Ala Leu Gly Leu Val Pro Ala Gly Val Lys Pro
            265                 270                 275 cat ccc ttc gtg ctc ccc gac ggg cgc gac tgg gcg cat ctc tcg ccc      1399
His Pro Phe Val Leu Pro Asp Gly Arg Asp Trp Ala His Leu Ser Pro
        280                 285                 290 acc gag aag cgc gaa cag gcg cgg ctg atg gaa gtc tat gcc gcg atg      1447
Thr Glu Lys Arg Glu Gln Ala Arg Leu Met Glu Val Tyr Ala Ala Met
    295                 300                 305 gtc gac cgg ctt gac cag aat gtc ggc aag gtg atc gcg cac ctc aag      1495
Val Asp Arg Leu Asp Gln Asn Val Gly Lys Val Ile Ala His Leu Lys
310                 315                 320                 325 gcg acc ggc cag tat gac aac acc atc atc ctg ttc ctc gcc gac aat      1543
Ala Thr Gly Gln Tyr Asp Asn Thr Ile Ile Leu Phe Leu Ala Asp Asn
                330                 335                 340 ggc gcc gaa ggg atc gac ctc gcc acc acc agg ctg ccc acc atg gcg      1591
Gly Ala Glu Gly Ile Asp Leu Ala Thr Thr Arg Leu Pro Thr Met Ala
            345                 350                 355 gca cgg ctg aag gcg gcg gac aat cgg ctc gac aat ctc ggc gcg gca      1639
Ala Arg Leu Lys Ala Ala Asp Asn Arg Leu Asp Asn Leu Gly Ala Ala
        360                 365                 370 agc tcc tac acc gcc tat ggt ccc ggc tgg gcg cag gcg gcg acc acg      1687
Ser Ser Tyr Thr Ala Tyr Gly Pro Gly Trp Ala Gln Ala Ala Thr Thr
    375                 380                 385 ccc tcc ttc ctc tac aag ggc ttc acc agc gag ggc ggc acc cgc gtc      1735
Pro Ser Phe Leu Tyr Lys Gly Phe Thr Ser Glu Gly Gly Thr Arg Val
390                 395                 400                 405 gcg gcg ttc ctc tcc tat ccc ggc tgg aag cgg cag ggc ggg atc agc      1783
Ala Ala Phe Leu Ser Tyr Pro Gly Trp Lys Arg Gln Gly Gly Ile Ser
                410                 415                 420 cat gcc tat ggc acg gtg atg gac gtg gtg ccg acg ctg gtc gag gcg      1831
His Ala Tyr Gly Thr Val Met Asp Val Val Pro Thr Leu Val Glu Ala
            425                 430                 435 gcc ggc ggc cac tgg cgg ggc agc agc tat ggc ggc cgt acg gtg cag      1879
Ala Gly Gly His Trp Arg Gly Ser Ser Tyr Gly Gly Arg Thr Val Gln
        440                 445                 450 ccg gtg cgc ggg agc agc tgg ctt ccc tat ctg cgt ggg cag tcc aag      1927
Pro Val Arg Gly Ser Ser Trp Leu Pro Tyr Leu Arg Gly Gln Ser Lys
    455                 460                 465 gcg gtg cat ggg ccg aaa gag atc gtc ggc acc gag ttg ttc ggc cgc      1975
Ala Val His Gly Pro Lys Glu Ile Val Gly Thr Glu Leu Phe Gly Arg
470                 475                 480                 485 cgc gcg atc cgg cag ggc gat tgg aag atc atc gat ctc ggc gac ggc      2023
Arg Ala Ile Arg Gln Gly Asp Trp Lys Ile Ile Asp Leu Gly Asp Gly
                490                 495                 500
```

-continued

```
tgg aag ctc tac aat ctg gcc gag gat ccc ggc gag acc cgc gac cgc     2071
Trp Lys Leu Tyr Asn Leu Ala Glu Asp Pro Gly Glu Thr Arg Asp Arg
        505                 510                 515 gcc gcc gac cag ccc gcc cgg ttg aag acg ctg gtc gcg gcc tgg gat     2119
Ala Ala Asp Gln Pro Ala Arg Leu Lys Thr Leu Val Ala Ala Trp Asp
    520                 525                 530 gcc tat gcc aag ggc gcg ggc gtg gtg atg cag tcc acc ccg gcg acc     2167
Ala Tyr Ala Lys Gly Ala Gly Val Val Met Gln Ser Thr Pro Ala Thr
535                 540                 545 ttc ccg tga agccgatcgc gctcctcgcg ctcgcgccgc tggccgggct             2216
Phe Pro  *
550 gccgctgctc tgggcgacgc gcccggcagc ggcacctacc ccgccggcc cgccacgggt   2276
gtgcgcgggc agccatctcg accggccggt gcgcattccc gccagccgct tcgtgatggg   2336
cagcagccgc tattatcccg aggaaggccc gcccaccgaa accgaggtgc ggcgttcga    2396
catcgacgca cacgaggtca ccaaccgcca gttcgcgacc ttcgtggctg caaccggcta   2456
tcgcaccgaa gcgagaaagc ccggcggcgg tgccttcgtg ttcgtaccgc ccaagaccgc   2516
gatcgacgaa cccgatccac gccgctggtg gcgtttcgtg cccggcgcaa actggcggca   2576
tcccgagggg ccgggcagca gcatcgccgg gcatgaggag gagcccgtgg tcgccgtcac   2636
cttcgtcgat gcccaggcct atgcccgctg ggcgggtcgt gcactgccga gcgaggagca   2696
gttcgaggcg gccgcgcgtg ttggcctcac cgatccggac gcggagccca accccgacca   2756
ggcgaacacc tggcagggca gcttccccaa catgaacgcc aagcgcgacg gctatacggg   2816
tcgtgcgcct gccggctgct tcaagccgaa cggggctggt gcctatgacc tgatcggcaa   2876
tgtctgggaa tggaccgaga gctggtatct gcccggccac gcgccgttcg cggtcggcga   2936
cggatcgccc ggcaacccga gcttcgatcc gcgccagccc gaggcgaagg cgcgcgtgat   2996
caagggcggc tcctatctct gcgcgaacaa ctattgcgcc cgctaccgcc ctgccgcccg   3056
ccacgcacaa gaggagacgc tcgccgcctc gcatctggga tttcggacgg tgagccggtc   3116
cgcgttcgat ctcgcgaccg acgcgagcgg gcacgcccgc cccgcccgtt cgccgtcctc   3176
gagggcgcaa ggccctgccc tctaatcgaa tcgctgatgg cgggcccgtc cgagaccccg   3236
catgatggtc gcgc                                                     3250
```

<210> SEQ ID NO 2
<211> LENGTH: 551
<212> TYPE: PRT
<213> ORGANISM: Sphingomonas elodea

<400> SEQUENCE: 2

```
Met Arg Leu Arg Leu Thr Ala Leu Leu Leu Leu Leu Pro Ser Pro
1               5                   10                  15

Ala Val Val Ala Gln Asp Lys Pro His Pro Ala Pro Pro Lys Arg
            20                  25                  30

Pro Asn Ile Leu Ile Ile Val Ala Asp Asp Leu Gly Tyr Ser Asp Leu
        35                  40                  45

Gly Ala Phe Gly Gly Glu Ile His Thr Pro Asn Leu Asp Ala Leu Ala
    50                  55                  60

Glu His Gly Leu Arg Leu Thr Gly Phe His Ala Pro Thr Cys Ser
65                  70                  75                  80

Pro Thr Arg Ser Met Leu Leu Ser Gly Thr Asp Asn His Leu Ala Gly
                85                  90                  95
```

```
Leu Gly Asn Met Ala Glu Leu Val Ala Pro Asn Gln Ile Gly Lys Pro
            100                 105                 110

Gly Tyr Gln Gly Tyr Leu Pro Asp Val Val Thr Leu Ala Glu Arg
        115                 120                 125

Leu Arg Asp Leu Gly Tyr Ala Thr Ala Met Ser Gly Lys Trp His Leu
    130                 135                 140

Gly Thr Arg Pro Gln Asp Asp Pro Thr Arg His Gly Phe Asp Gln Ala
145                 150                 155                 160

Phe Thr Leu Leu Gln Gly Gly Ala Asn His Phe Gly Ile Asp Ala Thr
                165                 170                 175

Ala Thr Pro Leu Pro Gly Gln Ala Thr Tyr Arg Glu Asn Gly Val Thr
            180                 185                 190

Leu Pro Asn Leu Pro Lys Asp Phe Tyr Ser Ser Asp Ala Tyr Ala Ala
        195                 200                 205

Lys Leu Ile Gly Phe Leu Gly Lys Thr Asp Pro Ala Lys Pro Phe Phe
    210                 215                 220

Ala Tyr Leu Thr Phe Thr Ala Pro His Trp Pro Leu Gln Ala Leu Pro
225                 230                 235                 240

Glu Asp Ile Ala Lys Tyr Arg Gly Arg Tyr Asp Ala Gly Phe Glu Val
                245                 250                 255

Leu Gln Ala Glu Arg Leu Lys Arg Gln Gln Ala Leu Gly Leu Val Pro
            260                 265                 270

Ala Gly Val Lys Pro His Pro Phe Val Leu Pro Asp Gly Arg Asp Trp
        275                 280                 285

Ala His Leu Ser Pro Thr Glu Lys Arg Glu Gln Ala Arg Leu Met Glu
    290                 295                 300

Val Tyr Ala Ala Met Val Asp Arg Leu Asp Gln Asn Val Gly Lys Val
305                 310                 315                 320

Ile Ala His Leu Lys Ala Thr Gly Gln Tyr Asp Asn Thr Ile Ile Leu
                325                 330                 335

Phe Leu Ala Asp Asn Gly Ala Glu Gly Ile Asp Leu Ala Thr Thr Arg
            340                 345                 350

Leu Pro Thr Met Ala Ala Arg Leu Lys Ala Ala Asp Asn Arg Leu Asp
        355                 360                 365

Asn Leu Gly Ala Ala Ser Ser Tyr Thr Ala Tyr Gly Pro Gly Trp Ala
    370                 375                 380

Gln Ala Ala Thr Thr Pro Ser Phe Leu Tyr Lys Gly Phe Thr Ser Glu
385                 390                 395                 400

Gly Gly Thr Arg Val Ala Ala Phe Leu Ser Tyr Pro Gly Trp Lys Arg
                405                 410                 415

Gln Gly Gly Ile Ser His Ala Tyr Gly Thr Val Met Asp Val Val Pro
            420                 425                 430

Thr Leu Val Glu Ala Ala Gly His Trp Arg Gly Ser Ser Tyr Gly
        435                 440                 445

Gly Arg Thr Val Gln Pro Val Arg Gly Ser Ser Trp Leu Pro Tyr Leu
    450                 455                 460

Arg Gly Gln Ser Lys Ala Val His Gly Pro Lys Glu Ile Val Gly Thr
465                 470                 475                 480

Glu Leu Phe Gly Arg Arg Ala Ile Arg Gln Gly Asp Trp Lys Ile Ile
                485                 490                 495

Asp Leu Gly Asp Gly Trp Lys Leu Tyr Asn Leu Ala Glu Asp Pro Gly
            500                 505                 510

Glu Thr Arg Asp Arg Ala Ala Asp Gln Pro Ala Arg Leu Lys Thr Leu
```

-continued

```
            515                 520                 525
Val Ala Ala Trp Asp Ala Tyr Ala Lys Gly Ala Gly Val Val Met Gln
    530                 535                 540

Ser Thr Pro Ala Thr Phe Pro
545                 550
```

<210> SEQ ID NO 3
<211> LENGTH: 1624
<212> TYPE: DNA
<213> ORGANISM: Sphingomonas elodea

<400> SEQUENCE: 3

| | | | | |
|---|---|---|---|---|
| tccacaccaa | cgccttcgac | tatgtccagc | aacgccccga | ggcgaccagc gagcaggtcc | 60 |
| gccgtcaccg | cgaagtgttc | gcctccacgg | cgtacgagac | cgagcatccg gtggtgcgcg | 120 |
| tccatccggt | gaccggcgag | aagctgctgc | tgctcggcag | cttcgtgaag agcttcgtcg | 180 |
| ggttcagccg | cgaggatttc | tcccggctgt | tcggcatcct | gcaggatcat gcgaccaagc | 240 |
| ccgagaacac | ggtgcgctgg | cgctggagcc | cgggcgatgt | ggcgatctgg acaaccgcg | 300 |
| ccacccagca | ccgcgccatc | gcggacttcg | gcaagcacgc | cgccatctg cgccgggcga | 360 |
| cgatcgccgg | cgacgtgccg | cgcggcgtcg | acggcaagcc | cagccgggtg ctcaagcccg | 420 |
| agccggtcgc | cgcagtcgaa | gccgccgccg | cctgaacttc | ccgtgcctgg gccgcgctcc | 480 |
| cctcggggaa | gcgcggctct | cttttccgga | caatccccag | tctagatcca ccccggcgac | 540 |
| cttcccgtga | agccgatcgc | gctcctcgcg | ctcgcgccgc | tggccgggct gccgctgctc | 600 |
| tgggcgacgc | gcccggcagc | ggcacctacc | cccgccggcc | cgccacgggt gtgcgcgggc | 660 |
| agccatctcg | accggccggt | gcgcattccc | gccagccgct | tcgtgatggg cagcagccgc | 720 |
| tattatcccg | aggaaggccc | gcccaccgaa | accgaggtgc | cggcgttcga catcgacgca | 780 |
| cacgaggtca | ccaaccgcca | gttcgcgacc | ttcgtggctg | caaccggcta tcgcaccgaa | 840 |
| gcggagaagc | ccggcggcgg | tgccttcgtg | ttcgtaccgc | ccaagaccgc gatcgacgaa | 900 |
| cccgatccac | gccgctggtg | gcgtttcgtg | cccggcgcaa | actggcggca tcccgagggg | 960 |
| ccgggcagca | gcatcgccgg | gcatgaggag | gagcccgtgg | tcgccgtcac cttcgtcgat | 1020 |
| gcccaggcct | atgcccgctg | ggcgggtcgt | gcactgccga | gcgaggagca gttcgaggcg | 1080 |
| gccgcgcgtg | ttggcctcac | cgatccggac | gcggagccca | accccgacca ggcgaacacc | 1140 |
| tggcagggca | gcttcccaa | catgaacgcc | aagcgcgacg | gctatacggg tcgtgcgcct | 1200 |
| gccggctgct | tcaagccgaa | cggggctggt | gcctatgacc | tgatcggcaa tgtctgggaa | 1260 |
| tggaccgaga | gctggtatct | gcccggccac | gcgccgttcg | cggtcggcga cggatcgccc | 1320 |
| ggcaacccga | gcttcgatcc | gcgccagccc | gaggcgaagg | cgcgcgtgat caagggcggc | 1380 |
| tcctatctct | gcgcgaacaa | ctattgcgcc | cgctaccgcc | ctgccgcccg ccacgcacaa | 1440 |
| gaggagacgc | tcgccgcctc | gcatctggga | tttcggacgg | tgagccggtc cgcgttcgat | 1500 |
| ctcgcgaccg | acgcgagcgg | gcacgcccgc | cccgcccgtt | cgccgtcctc gagggcgcaa | 1560 |
| ggccctgccc | tctaatcgaa | tcgctgatgg | cgggcccgtc | cgagacccccg catgatggtc | 1620 |
| gcgc | | | | | 1624 |

<210> SEQ ID NO 4
<211> LENGTH: 4716
<212> TYPE: DNA
<213> ORGANISM: Sphingomonas elodea
<220> FEATURE:
<221> NAME/KEY: CDS -continued

<222> LOCATION: (1591)...(3450)

<400> SEQUENCE: 4

| | | |
|---|---|---|
| ctgcgtgatc ggcgccgtca cccgtgccgc gacgtcgacc ggctcgcgcg cctcgacgaa | 60 |
| gccggtggca tagacgacat cggcggccgg gccgatccgg acgggcgtgc cgaccaccgc | 120 |
| gagcggctgg cggagccaga acaggccgcc ggcgcccgcc ccgcgatcg ccaccggaac | 180 |
| cagccaatag atgcgccgca accgcatgtc cgtctccagc ctcgtgcctg tgctaccagc | 240 |
| agcggccggg ggtggtaact agggaggctt ccgcagcttc cctaactgga acgtggccgc | 300 |
| tatgcgcaac gttcgcccgg gcggtcgcca gcgacagccc ggccgcccga tcccgcccgg | 360 |
| cgcgctgccg gcgcagtatg gaaaccaccg cccggcatga ctcgcgtcct cgatcgttac | 420 |
| cgcgccctcg tctccgccgg cgagcttcgc ccgatcgtg agcaggaagc cgccgccgcc | 480 |
| cgtctcgacg ccctggccgc ggaactgcag gccgccccgc gcaagggcag cgtgttgtgg | 540 |
| aagcttaccg gccgcaagcc ggcggtgccg cgcgggctgt atctgtgggg cgatgtcggc | 600 |
| cgcggcaagt cgatgctgat ggacctgttc tacgacagcc tcgacatccg ccggaagcgc | 660 |
| cgcgtccatt ttcacgaatt catgctcgag gtgcatgagc ggctgaacgt cgagcggcag | 720 |
| aaggataccg ccgatccggt ggtcgccgtc gccgatgcgc tcgccagcga cacgcgcctg | 780 |
| ctcgcctttg acgaactggt ggtgaacaat ccgcccgacg cgatgatcct ctcgaggttg | 840 |
| ttcaccgcga tgatggcaca cgggctcacg gtggtcgcca cctccaatcg cccgcccaag | 900 |
| gatctctaca aggacgggct caaccgccag ctgttcctgc ccttcatcga cctgatcggc | 960 |
| gagaagatgg acgtgctcgc gctcaacggc ccggtcgact atcgccgcga ccggctgggc | 1020 |
| agcgtacaca cgtggcttgt gccgaacggg cccgaagcca ccgccaccct ctccgcggcc | 1080 |
| ttttccgcc tcaccgacta tccggtcgag gaccgcgccc gcgtgccgtc ctgccaggtg | 1140 |
| ccgatccccg gcggccgcga gatcctggtg ccgaaatgcg tgaagggcgt cgccgtcttc | 1200 |
| tcgttcaagc ggctgtgcgg cgaagcgcgg ggtgcgccgg actatctcgc catcgcacgg | 1260 |
| cgcttccata ccgtgatcct ggtcggcatc ccaaagctgg gaccggaaaa tcggaacgag | 1320 |
| gccgcccgct tcgtcacgct ggtcgacgcg ctctacgagc acaaggtgaa gctgctcgcc | 1380 |
| gccgccaatg ccgaacccga acatctctac gagagtggcg acgggcggtt cgagttcgag | 1440 |
| cgcaccgtgt cgcgcctgct cgagatgcag tccgacgact atctggccaa aggccatgga | 1500 |
| caggattgat cagaccacgt tgtaagtcca ttctcccgtt ctacaatgac atcgggctcc | 1560 |
| gggttttccc ggaggaacag ggagaagatg atg cgg cga ttg cgc ctt ctc gca<br>                                                        Met Arg Arg Leu Arg Leu Leu Ala<br>                                                          1                  5 | 1614 |
| gcc atg ggg ttt gcg tgg ctc gga ata tcc tcg gcc tgg gcg cag ccc<br>Ala Met Gly Phe Ala Trp Leu Gly Ile Ser Ser Ala Trp Ala Gln Pro<br>    10                      15                      20 | 1662 |
| gtg ctc gtc gcg gcg gac ctc cgc cag cag cag agc ctc gac ggg ccg<br>Val Leu Val Ala Ala Asp Leu Arg Gln Gln Gln Ser Leu Asp Gly Pro<br>25                      30                      35                      40 | 1710 |
| tgg cac tgg tcg atc gat cca tac cgc gat ggt ctg gcc ggt ttc cat<br>Trp His Trp Ser Ile Asp Pro Tyr Arg Asp Gly Leu Ala Gly Phe His<br>                      45                      50                      55 | 1758 |
| ggc gaa ccg ccc aac cag cgc acc aac cgc gcc gcc gac gtg atc ccc<br>Gly Glu Pro Pro Asn Gln Arg Thr Asn Arg Ala Ala Asp Val Ile Pro<br>                60                      65                      70 | 1806 |
| gcc gag gtg atg cag gcc aag ccg cgc acc ttc ttc gaa tat gac atg<br>Ala Glu Val Met Gln Ala Lys Pro Arg Thr Phe Phe Glu Tyr Asp Met<br>    75                      80                      85 | 1854 |

```
                                             -continued cag cag tcg ccg gta gcc agc ctg ccg gga tcg tgg atc ggc cat tcg    1902
Gln Gln Ser Pro Val Ala Ser Leu Pro Gly Ser Trp Ile Gly His Ser
         90                  95                 100 ccc gag atg cgg ctg tac cag ggg ctg gtc tgg tac cag cgc gac ttc    1950
Pro Glu Met Arg Leu Tyr Gln Gly Leu Val Trp Tyr Gln Arg Asp Phe
105                 110                 115                 120 acc gcg gcg gca ccc aag ccc ggt aac cgc gtg ttc ctg cgc atc ggc    1998
Thr Ala Ala Ala Pro Lys Pro Gly Asn Arg Val Phe Leu Arg Ile Gly
                125                 130                 135 gcg gcc gaa tat cgc tcc tat gtg tat ctc aac ggc aag ccg ctg ggc    2046
Ala Ala Glu Tyr Arg Ser Tyr Val Tyr Leu Asn Gly Lys Pro Leu Gly
            140                 145                 150 gag cat cgc ggc ggc tac acg ccg ttc gcc ttc gag gtc acc aag ctg    2094
Glu His Arg Gly Gly Tyr Thr Pro Phe Ala Phe Glu Val Thr Lys Leu
        155                 160                 165 ctg cgc ccg ggt cgc aac cag gtg acg atc ggc gtc gat tcg gtg cgc    2142
Leu Arg Pro Gly Arg Asn Gln Val Thr Ile Gly Val Asp Ser Val Arg
    170                 175                 180 acc gcc aac gac gtg ccg cca ccg gtg acc gat tgg gag acc tat ggc    2190
Thr Ala Asn Asp Val Pro Pro Pro Val Thr Asp Trp Glu Thr Tyr Gly
185                 190                 195                 200 ggc atc acc cgc agc gtc acg ctt gtc acc gtg ccc gat acc tat gtc    2238
Gly Ile Thr Arg Ser Val Thr Leu Val Thr Val Pro Asp Thr Tyr Val
                205                 210                 215 gac gac gcc ttc gtc cgc ctg acg ccg gac ggc acc cgc atc gcg gta    2286
Asp Asp Ala Phe Val Arg Leu Thr Pro Asp Gly Thr Arg Ile Ala Val
            220                 225                 230 tcg gtg aag ctc gaa ggg ccg gcg gcc gcg gga acg gcg gtc agg ttc    2334
Ser Val Lys Leu Glu Gly Pro Ala Ala Ala Gly Thr Ala Val Arg Phe
        235                 240                 245 cgc att ccg ggc ctc ggc gcc gtg ctc gac ggc aag acc gat ggc gag    2382
Arg Ile Pro Gly Leu Gly Ala Val Leu Asp Gly Lys Thr Asp Gly Glu
    250                 255                 260 ggc aaa tgg gac gcg acg ctg ccg gtg ccg cgt gcg ctg gtc cgc tgg    2430
Gly Lys Trp Asp Ala Thr Leu Pro Val Pro Arg Ala Leu Val Arg Trp
265                 270                 275                 280 tcg ccg gag aac ccg aag ctc tac gac atc gcc atc gac gcc ggc gcc    2478
Ser Pro Glu Asn Pro Lys Leu Tyr Asp Ile Ala Ile Asp Ala Gly Ala
                285                 290                 295 gat cat ttc gcc gat cgc atg ggc ttc cgc acc atc gcg gtg aag ggc    2526
Asp His Phe Ala Asp Arg Met Gly Phe Arg Thr Ile Ala Val Lys Gly
            300                 305                 310 gcc gac atc ctg ctc aac ggc aag ccg atc ttc ctg cgc ggc atc tcg    2574
Ala Asp Ile Leu Leu Asn Gly Lys Pro Ile Phe Leu Arg Gly Ile Ser
        315                 320                 325 atg cac gag gaa gaa ctg ggc gcc gat ccg gtt cgc gcg atg acg ccg    2622
Met His Glu Glu Glu Leu Gly Ala Asp Pro Val Arg Ala Met Thr Pro
    330                 335                 340 gca gcc gcc cgc gcc ctg ctg ggc gag atc aaa tat ggc ctg cac ggc    2670
Ala Ala Ala Arg Ala Leu Leu Gly Glu Ile Lys Tyr Gly Leu His Gly
345                 350                 355                 360 aat ttc gtg cgg ctg gcg cac tat ccg cac agc gag tcg acc acc cgc    2718
Asn Phe Val Arg Leu Ala His Tyr Pro His Ser Glu Ser Thr Thr Arg
                365                 370                 375 atg gcg gac gag atg ggc ctg gtg tgg agc gag gtg ccc ctc tac        2766
Met Ala Asp Glu Met Gly Leu Val Trp Ser Glu Val Pro Leu Tyr
            380                 385                 390 tgg ctg gtc aac tgg aac aac ccg gac acg ctg gcc gac gcc cgt cgc    2814
Trp Leu Val Asn Trp Asn Asn Pro Asp Thr Leu Ala Asp Ala Arg Arg
```

-continued

```
                     395                 400                 405
atc cag gcc gag aac atc cgc cgc gac cgc aac cgt gcc tcg gtc gtg       2862
Ile Gln Ala Glu Asn Ile Arg Arg Asp Arg Asn Arg Ala Ser Val Val
        410                 415                 420 ctg tgg agc gtc gcc aac gag acg ccg acc aac gat gcg cgc aac gcc       2910
Leu Trp Ser Val Ala Asn Glu Thr Pro Thr Asn Asp Ala Arg Asn Ala
425                 430                 435                 440 ttc ctg cgc acg atg atc gcc gat gtc cgc gcg ctc gac tcc agc cgt       2958
Phe Leu Arg Thr Met Ile Ala Asp Val Arg Ala Leu Asp Ser Ser Arg
                445                 450                 455 ctc gtc acc gcc gcg ctg ctc agc ggt cgc gag ggc aag agc atc atg       3006
Leu Val Thr Ala Ala Leu Leu Ser Gly Arg Glu Gly Lys Ser Ile Met
            460                 465                 470 aag atc gac gat ccg ctg gcc aac gac ctc gat gtc atg gcg atc aac       3054
Lys Ile Asp Asp Pro Leu Ala Asn Asp Leu Asp Val Met Ala Ile Asn
        475                 480                 485 acc tat aat ggt tgg tac tcc gac gac gcg ctg gag gat ctg gcc agc       3102
Thr Tyr Asn Gly Trp Tyr Ser Asp Asp Ala Leu Glu Asp Leu Ala Ser
    490                 495                 500 cag gaa tgg cgc gga ccg gcg aac aag ccg ctg atc ttc tcc gaa ttc       3150
Gln Glu Trp Arg Gly Pro Ala Asn Lys Pro Leu Ile Phe Ser Glu Phe
505                 510                 515                 520 ggc gcc gac gcc cgc gcc ggc tat cac gac ccg gtg gcg agc ccg cac       3198
Gly Ala Asp Ala Arg Ala Gly Tyr His Asp Pro Val Ala Ser Pro His
                525                 530                 535 aag ttc agc gag gag tat cag gcc gac tat tac cgc gcg aca ctg gcg       3246
Lys Phe Ser Glu Glu Tyr Gln Ala Asp Tyr Tyr Arg Ala Thr Leu Ala
            540                 545                 550 atg gcc gcc aag gtg ccg ttc ctg cgc ggc atg agc ccc tgg atc ctc       3294
Met Ala Ala Lys Val Pro Phe Leu Arg Gly Met Ser Pro Trp Ile Leu
        555                 560                 565 aag gac ttc cgc tcg ccg cgg cgc cag cac ccg atc tat cag cag ggc       3342
Lys Asp Phe Arg Ser Pro Arg Arg Gln His Pro Ile Tyr Gln Gln Gly
    570                 575                 580 tgg aac cgc aag ggc ctg atc tcc gag aca ggc cag cac aag ctg gcg       3390
Trp Asn Arg Lys Gly Leu Ile Ser Glu Thr Gly Gln His Lys Leu Ala
585                 590                 595                 600 ttc gat gtg ctc gca ggc gat tat gcc aag cgc gag gct gcg gac gcg       3438
Phe Asp Val Leu Ala Gly Asp Tyr Ala Lys Arg Glu Ala Ala Asp Ala
                605                 610                 615 gcg aag aag tga ctgtccaggc ccctctcgca tgcgggaggg gcctagggtg           3490
Ala Lys Lys * cggaggccgg tgtcctctgc acggttggcg ggaagccgca gggaagtcgc cagaatcccg     3550
cagcggcgcg aaaccgagca aaatactctc tattgctctt gcaatgaatt gcaaagata     3610 atcctgcacc tatcccccaa cacgggttgc agcgtcgcta ttataggcct atcccgcccc     3670
cgctttcgcg gcgcatcgtg atgcggccgc tttgcttgga tccaaccaag gagattccat     3730
ggctcgcaag aagatcgcgc tgatcggctc cggcatgatc ggtggcaccc tcgcgcacct     3790
cgctgcaatc aaggaactgg gcgatatcgt cctgttcgac attgccgagg gcacgccgca     3850
gggcaaggcg ctcgacatcg cacagtccgg accggtcgaa ggcttcgatg ccaacctcaa     3910
gggcgcgaac agctacgagg acattgcggg gccgacgtc tgcatcgtca ccgccggtat     3970
cccgcgcaag ccgggcatga ccgcgacga tcttctcaag accaacctgg gcgtgatgaa     4030
ggccgtgggc gagggcatcg ccgcgcacg gcccgacgcg ttcgtgatct gcatcaccaa     4090
cccgctcgac gcgatggtgt gggcgctgcg cgagttctcg ggcctgccgc accagaaggt     4150
```

```
cgtcggcatg gccggcgtgc tcgactcggc gcgcttccgc cacttcctcg ccgaggaatt    4210
caacgtctcg gtcgaggacg tcaccgcctt cgtgctgggg ggacacggcg acaccatggt    4270
cccggtgatc gagtattcga ccgtcgccgg catcccggtg cccgacctga tcaagatggg    4330
ctggtccacc caggagcgca tcgacgccat cgtcgcgcg acccgctcgg gcggcggcga    4390
gatcgtcgcg ctgctcaaga ccggctcggc ctattatgcg ccggccacca gcgcgatcgc    4450
gatggccgag agctatctga aggacaagaa gcgcctgctt ccctgtgccg cgcacctcac    4510
cggccagtac ggcgtcgacg atctgtacgt cggcgtgccg atcgtcatcg gcaaggacgg    4570
cgtcgagcgc atcgtcgaga tcgagctgaa cgccacggcg aagcagaatt tcgacgtctc    4630
ggtcgatgcg gtcaaggaac tggtcgcagc atgcaagtcg atcgacgcct cgctcgcctg    4690
atcctacccg cgctcgtggc ggtgcc                                          4716

<210> SEQ ID NO 5
<211> LENGTH: 619
<212> TYPE: PRT
<213> ORGANISM: Sphingomonas elodea

<400> SEQUENCE: 5

Met Arg Arg Leu Arg Leu Leu Ala Ala Met Gly Phe Ala Trp Leu Gly
  1               5                  10                  15

Ile Ser Ser Ala Trp Ala Gln Pro Val Leu Val Ala Ala Asp Leu Arg
             20                  25                  30

Gln Gln Gln Ser Leu Asp Gly Pro Trp His Trp Ser Ile Asp Pro Tyr
         35                  40                  45

Arg Asp Gly Leu Ala Gly Phe His Gly Glu Pro Pro Asn Gln Arg Thr
     50                  55                  60

Asn Arg Ala Ala Asp Val Ile Pro Ala Glu Val Met Gln Ala Lys Pro
 65                  70                  75                  80

Arg Thr Phe Phe Glu Tyr Asp Met Gln Gln Ser Pro Val Ala Ser Leu
                 85                  90                  95

Pro Gly Ser Trp Ile Gly His Ser Pro Glu Met Arg Leu Tyr Gln Gly
            100                 105                 110

Leu Val Trp Tyr Gln Arg Asp Phe Thr Ala Ala Pro Lys Pro Gly
        115                 120                 125

Asn Arg Val Phe Leu Arg Ile Gly Ala Ala Glu Tyr Arg Ser Tyr Val
    130                 135                 140

Tyr Leu Asn Gly Lys Pro Leu Gly Glu His Arg Gly Gly Tyr Thr Pro
145                 150                 155                 160

Phe Ala Phe Glu Val Thr Lys Leu Leu Arg Pro Gly Arg Asn Gln Val
                165                 170                 175

Thr Ile Gly Val Asp Ser Val Arg Thr Ala Asn Asp Val Pro Pro
            180                 185                 190

Val Thr Asp Trp Glu Thr Tyr Gly Gly Ile Thr Arg Ser Val Thr Leu
        195                 200                 205

Val Thr Val Pro Asp Thr Tyr Val Asp Ala Phe Val Arg Leu Thr
    210                 215                 220

Pro Asp Gly Thr Arg Ile Ala Val Ser Val Lys Leu Glu Gly Pro Ala
225                 230                 235                 240

Ala Ala Gly Thr Ala Val Arg Phe Arg Ile Pro Gly Leu Gly Ala Val
                245                 250                 255

Leu Asp Gly Lys Thr Asp Gly Glu Gly Lys Trp Asp Ala Thr Leu Pro
            260                 265                 270
```

Val Pro Arg Ala Leu Val Arg Trp Ser Pro Glu Asn Pro Lys Leu Tyr
        275                 280                 285

Asp Ile Ala Ile Asp Ala Gly Ala Asp His Phe Ala Asp Arg Met Gly
        290                 295                 300

Phe Arg Thr Ile Ala Val Lys Gly Ala Asp Ile Leu Leu Asn Gly Lys
305                 310                 315                 320

Pro Ile Phe Leu Arg Gly Ile Ser Met His Glu Glu Leu Gly Ala
                325                 330                 335

Asp Pro Val Arg Ala Met Thr Pro Ala Ala Arg Ala Leu Leu Gly
            340                 345                 350

Glu Ile Lys Tyr Gly Leu His Gly Asn Phe Val Arg Leu Ala His Tyr
        355                 360                 365

Pro His Ser Glu Ser Thr Thr Arg Met Ala Asp Glu Met Gly Leu Leu
        370                 375                 380

Val Trp Ser Glu Val Pro Leu Tyr Trp Leu Val Asn Trp Asn Asn Pro
385                 390                 395                 400

Asp Thr Leu Ala Asp Ala Arg Arg Ile Gln Ala Glu Asn Ile Arg Arg
                405                 410                 415

Asp Arg Asn Arg Ala Ser Val Val Leu Trp Ser Val Ala Asn Glu Thr
            420                 425                 430

Pro Thr Asn Asp Ala Arg Asn Ala Phe Leu Arg Thr Met Ile Ala Asp
        435                 440                 445

Val Arg Ala Leu Asp Ser Ser Arg Leu Val Thr Ala Ala Leu Leu Ser
450                 455                 460

Gly Arg Glu Gly Lys Ser Ile Met Lys Ile Asp Asp Pro Leu Ala Asn
465                 470                 475                 480

Asp Leu Asp Val Met Ala Ile Asn Thr Tyr Asn Gly Trp Tyr Ser Asp
                485                 490                 495

Asp Ala Leu Glu Asp Leu Ala Ser Gln Glu Trp Arg Gly Pro Ala Asn
            500                 505                 510

Lys Pro Leu Ile Phe Ser Glu Phe Gly Ala Asp Ala Arg Ala Gly Tyr
        515                 520                 525

His Asp Pro Val Ala Ser Pro His Lys Phe Ser Glu Glu Tyr Gln Ala
        530                 535                 540

Asp Tyr Tyr Arg Ala Thr Leu Ala Met Ala Ala Lys Val Pro Phe Leu
545                 550                 555                 560

Arg Gly Met Ser Pro Trp Ile Leu Lys Asp Phe Arg Ser Pro Arg Arg
                565                 570                 575

Gln His Pro Ile Tyr Gln Gln Gly Trp Asn Arg Lys Gly Leu Ile Ser
            580                 585                 590

Glu Thr Gly Gln His Lys Leu Ala Phe Asp Val Leu Ala Gly Asp Tyr
        595                 600                 605

Ala Lys Arg Glu Ala Ala Asp Ala Ala Lys Lys
    610                 615

<210> SEQ ID NO 6
<211> LENGTH: 2862
<212> TYPE: DNA
<213> ORGANISM: Sphingomonas elodea

<400> SEQUENCE: 6
ctgcgtgatc ggcgccgtca cccgtgccgc gacgtcgacc ggctcgcgcg cctcgacgaa      60
gccggtggca tagacgacat cggcggccgg gccgatccgg acgggcgtgc cgaccaccgc     120
gagcggctgg cggagccaga acaggccgcc ggcgcccgcc ccgcgatcg ccaccggaac     180

```
cagccaatag atgcgccgca accgcatgtc cgtctccagc ctcgtgcctg tgctaccagc      240
agcggccggg ggtggtaact agggaggctt ccgcagcttc cctaactgga acgtggccgc      300
tatgcgcaac gttcgcccgg gcggtcgcca gcgacagccc ggccgcccga tcccgcccgg      360
cgcgctgccg gcgcagtatg gaaaccaccg cccggcatga ctcgcgtcct cgatcgttac      420
cgcgccctcg tctccgccgg cgagcttcgc cccgatcgtg agcaggaagc cgccgccgcc      480
cgtctcgacg ccctggccgc ggaactgcag gccgccccgc gcaagggcag cgtgttgtgg      540
aagcttaccg gccgcaagcc ggcggtgccg cgcgggctgt atctgtgggg cgatgtcggc      600
cgcggcaagt cgatgctgat ggacctgttc tacgacagcc tcgacatccg ccggaagcgc      660
cgcgtccatt ttcacgaatt catgctcgag gtgcatgagc ggctgaacgt cgagcggcag      720
aaggataccg ccgatccggt ggtcgccgtc gccgatgcgc tcgccagcga cacgcgcctg      780
ctcgcctttg acgaactggt ggtgaacaat ccgcccgacg cgatgatcct ctcgaggttg      840
ttcaccgcga tgatggcaca cgggctcacg gtggtcgcca cctccaatcg cccgcccaag      900
gatctctaca aggacgggct caaccgccag ctgttcctgc ccttcatcga cctgatcggc      960
gagaagatgg acgtgctcgc gctcaacggc ccggtcgact atcgccgcga ccggctgggc     1020
agcgtacaca cgtggcttgt gccgaacggg cccgaagcca ccgccaccct ctccgcggcc     1080
tttttccgcc tcaccgacta tccggtcgag gaccgcgccc gcgtgccgtc ctgccaggtg     1140
ccgatccccg gcggccgcga gatcctggtc cgaaatgcg tgaagggcgt cgccgtcttc     1200
tcgttcaagc ggctgtgcgg cgaagcgcgg ggtgcgccgg actatctcgc catcgcacgg     1260
cgcttccata ccgtgatcct ggtcggcatc ccaaagctgg accggaaaa tcggaacgag     1320 gccgcccgct tcgtcacgct ggtcgacgcg ctctacgagc acaaggtgaa gctgctcgcc     1380
gccgccaatg ccgaacccga acatctctac gagagtggcg acgggcggtt cgagttcgag     1440
cgcaccgtgt cgcgcctgct cgagatgcag tccgacgact atctggccaa aggccatgga     1500
caggattgat cagaccacgt tgtaagtcca ttctcccgtt ctacaatgac atcgggctcc     1560
gggttttccc ggaggaacag ggagaagtct agatgactgt ccaggcccct ctcgcatgcg     1620 ggagggggcct agggtgcgga ggccggtgtc ctctgcacgg ttggcgggaa gccgcaggga     1680
agtcgccaga atcccgcagc ggcgcgaaac cgagcaaaat actctctatt gctcttgcga     1740
atgaattgca aagataatcc tgcacctatc ccccaacacg ggttgcagcg tcgctattat     1800
aggcctatcc cgcccccgct ttcgcggcgc atcgtgatgc ggccgctttg cttggatcca     1860
accaaggaga ttccatggct cgcaagaaga tcgcgctgat cggctccggc atgatcggtg     1920
gcaccctcgc gcacctcgct gcaatcaagg aactgggcga tatcgtcctg ttcgacattg     1980
ccgagggcac gccgcagggc aaggcgctcg acatcgcaca gtccggaccg gtcgaaggct     2040
tcgatgccaa cctcaagggc gcgaacagct acgaggacat tgcgggcgcc gacgtctgca     2100
tcgtcaccgc cggtatcccg cgcaagccgg gcatgagccg cgacgatctt ctcaagacca     2160
acctgggcgt gatgaaggcc gtgggcgagg gcatcgccgc gcacgcgccc gacgcgttcg     2220
tgatctgcat caccaacccg ctcgacgcga tggtgtgggc gctgcgcgag ttctcgggcc     2280
tgccgcacca gaaggtcgtc ggcatggccg gcgtgctcga ctcggcgcgc ttccgccact     2340
tcctcgccga ggaattcaac gtctcggtcg aggacgtcac cgccttcgtg ctgggcggac     2400
acggcgacac catggtcccg gtgatcgagt attcgaccgt cgccggcatc ccggtgcccg     2460
acctgatcaa gatgggctgg tccacccagg agcgcatcga cgccatcgtc gcgcgcaccc     2520
```

```
gctcgggcgg cggcgagatc gtcgcgctgc tcaagaccgg ctcggcctat tatgcgccgg      2580
ccaccagcgc gatcgcgatg gccgagagct atctgaagga caagaagcgc ctgcttccct      2640
gtgccgcgca cctcaccggc cagtacggcg tcgacgatct gtacgtcggc gtgccgatcg      2700
tcatcggcaa ggacggcgtc gagcgcatcg tcgagatcga gctgaacgcc acggcgaagc      2760
agaatttcga cgtctcggtc gatgcggtca aggaactggt cgcagcatgc aagtcgatcg      2820
acgcctcgct cgcctgatcc tacccgcgct cgtggcggtg cc                        2862

<210> SEQ ID NO 7
<211> LENGTH: 28
<212> TYPE: DNA
<213> ORGANISM: Sphingomonas elodea

<400> SEQUENCE: 7
aactgcagac acgtggcttg tgccgaac                                         28

<210> SEQ ID NO 8
<211> LENGTH: 32
<212> TYPE: DNA
<213> ORGANISM: Sphingomonas elodea

<400> SEQUENCE: 8
ggctctagac ttctccctgt tcctccggga aa                                    32

<210> SEQ ID NO 9
<211> LENGTH: 28
<212> TYPE: DNA
<213> ORGANISM: Sphingomonas elodea

<400> SEQUENCE: 9
tttctagatg actgtccagg cccctctc                                         28

<210> SEQ ID NO 10
<211> LENGTH: 28
<212> TYPE: DNA
<213> ORGANISM: Sphingomonas elodea

<400> SEQUENCE: 10
tcgagctcca atgtcctcgt agctgttc                                         28

<210> SEQ ID NO 11
<211> LENGTH: 28
<212> TYPE: DNA
<213> ORGANISM: Sphingomonas elodea

<400> SEQUENCE: 11
ccgagctcaa cgccttcgac tatgtcca                                         28

<210> SEQ ID NO 12
<211> LENGTH: 28
<212> TYPE: DNA
<213> ORGANISM: Sphingomonas elodea

<400> SEQUENCE: 12
cctctagact ggggattgtc cggaaaag                                         28

<210> SEQ ID NO 13
<211> LENGTH: 28
<212> TYPE: DNA
<213> ORGANISM: Sphingomonas elodea

<400> SEQUENCE: 13
```

```
cgtctagatc caccccggcg accttccc                                          28
```

<210> SEQ ID NO 14
<211> LENGTH: 32
<212> TYPE: DNA
<213> ORGANISM: Sphingomonas elodea

<400> SEQUENCE: 14

```
tatagcatgc ggcgaccacg ggctcctcct ca                                     32
```